United States Patent
Huang

(10) Patent No.: US 11,484,611 B2
(45) Date of Patent: *Nov. 1, 2022

(54) METHOD FOR STERILIZING BIOLOGICAL MATERIALS

(71) Applicant: FM&G Biomed Co., Ltd., Tainan (TW)

(72) Inventor: Lynn L. H. Huang, Tainan (TW)

(73) Assignee: FM&G Biomed Co., Ltd., Tainan (TW)

(*) Notice: Subject to any disclaimer, the term of this patent is extended or adjusted under 35 U.S.C. 154(b) by 0 days.

This patent is subject to a terminal disclaimer.

(21) Appl. No.: 16/357,919

(22) Filed: Mar. 19, 2019

(65) Prior Publication Data

US 2019/0209720 A1 Jul. 11, 2019

Related U.S. Application Data

(63) Continuation of application No. 13/326,391, filed on Dec. 15, 2011, now Pat. No. 10,232,064, which is a continuation-in-part of application No. 11/866,564, filed on Oct. 3, 2007, now abandoned.

(30) Foreign Application Priority Data

Oct. 4, 2006 (TW) .................. 095136924

(51) Int. Cl.
*A61L 2/20* (2006.01)
*A61L 2/00* (2006.01)

(52) U.S. Cl.
CPC ............ *A61L 2/0094* (2013.01); *A61L 2/202* (2013.01)

(58) Field of Classification Search
CPC ................... A61L 2/202; A61L 2/0094
See application file for complete search history.

(56) References Cited

U.S. PATENT DOCUMENTS

| | | |
|---|---|---|
| 4,182,663 A | 1/1980 | Vaseen |
| 5,460,962 A | 10/1995 | Kemp |
| 5,485,496 A | 1/1996 | Lee et al. |
| 5,700,426 A | 12/1997 | Schmitthaeusler et al. |
| 5,749,203 A | 5/1998 | McGowan, Jr. |
| 5,788,941 A | 8/1998 | Dalmasso et al. |
| 6,096,266 A | 8/2000 | Duroselle |

(Continued)

FOREIGN PATENT DOCUMENTS

| | | |
|---|---|---|
| CN | 1427729 | 7/2003 |
| TW | 061995 | 10/1984 |

(Continued)

OTHER PUBLICATIONS

Elizabeth Tiktopulo et al., "Denaturation of Type 1 Collagen Fibrils Is an Endothermic Process Accompanied by a Noticeable Change in the Partial Heat Capacity" Biochemistry vol. 37, pp. 8147-8152, 1998.

*Primary Examiner* — Kevin Joyner
(74) *Attorney, Agent, or Firm* — Cesari & McKenna, LLP

(57) ABSTRACT

A method for sterilizing biological materials is disclosed. A dehydrated biological material is put into a closed container. The closed container is then decompressed under a vacuum. Subsequently, 0.01 $g/m^3$ to 1000 $g/m^3$ of a sterilizing gas, i.e., pure ozone, is introduced into the container for a period of time until the biological material is sterilized.

20 Claims, 4 Drawing Sheets

1. autoclaved
2. ozone sterilized
3. untreated control 4. autoclaved
5. ozone sterilized
6. untreated control

(56) References Cited

U.S. PATENT DOCUMENTS

| | | |
|---|---|---|
| 2001/0018072 A1 | 8/2001 | Unger |
| 2003/0031581 A1 | 2/2003 | Miekka et al. |
| 2003/0058982 A1 | 3/2003 | Nagase et al. |
| 2004/0022666 A1 | 2/2004 | Biddle et al. |
| 2007/0065335 A1* | 3/2007 | Bedard .................. A61L 2/202 422/27 |

FOREIGN PATENT DOCUMENTS

| | | |
|---|---|---|
| TW | 115972 | 7/1989 |
| TW | 149465 | 3/1990 |
| TW | 145942 | 11/1990 |
| TW | 241193 | 2/1995 |
| TW | 310308 | 7/1997 |
| TW | 443932 | 7/2001 |
| TW | 474828 | 2/2002 |
| TW | 512064 | 12/2002 |
| WO | WO-0170279 | 9/2001 |

* cited by examiner 1. autoclaved
2. ozone sterilized
3. untreated control
4. autoclaved
5. ozone sterilized
6. untreated control 1. autoclaved
2. ozone sterilized
3. untreated control
4. autoclaved
5. ozone sterilized
6. untreated control

METHOD FOR STERILIZING BIOLOGICAL MATERIALS

CROSS REFERENCE TO RELATED APPLICATION

This application is a continuation of U.S. patent application Ser. No. 13/326,391, filed on Dec. 15, 2011, now U.S. Pat. No. 10,232,064, which is a continuation-in-part of U.S. patent application Ser. No. 11/866,564, filed on Oct. 3, 2007, which claims priority under 35 U.S.C. § 119(e) to Taiwan Patent Application No. 095136924. The contents of all prior applications are hereby incorporated by reference in their entirety.

BACKGROUND OF THE INVENTION

1. Field of the Invention

The present invention relates to a sterilizing method. More specifically, the present invention relates to a method for sterilizing biological materials employing ozone.

2. Description of Related Art

Typically, biological materials, which may refer to materials existing in or derived from living organisms, substantially comprise components, e.g., amino acids, peptides, proteins, polysaccharides, directly extracted from microorganisms, animals or plants. As biological materials possess excellent biocompatibility, they have potential for pharmaceutical and cosmetic applications, e.g., use as wound dressings and scaffolds for tissue engineering. Biological materials for use in humans or living organisms must be subjected to a strict sterilizing procedure. However, most biological materials are sensitive to high temperature sterilization, as they are prone to denaturation. As such, options for sterilizing biological materials are very restricted. Thus, there is a focus on determining how to sterilize biological materials without compromising their bioactivity.

There are several methods of sterilizing biological materials, as follows. (1) Sterilization with 75% ethanol: the biological material is immersed in 75% ethanol, and it must be reserved and delivered in moist state. However, the bioactive components are liable to be denatured in such a moist state. Moreover, it is uncertain whether ethanol is completely removed from the biological material by rinsing before use. (2) Sterilization with γ-irradiation, disclosed in U.S. Pat. No. 5,485,496, and Taiwan Pat. Nos. 145,942, and 115,972: this commonly applied method employs γ-ray to irradiate a biological material. However, the energy of the γ-ray is so high that some chemical structures within the biological material are destroyed, resulting in weakening of mechanical strength of the biological material. In addition, γ-ray irradiation is hazardous to humans so it has to be operated in a specific place, resulting in inconvenient usage. (3) Sterilization with ultraviolet light, as disclosed in Taiwan Pat. No. 474,828: this method employs ultraviolet light to irradiate a biological material for sterilization. Nevertheless, ultraviolet light minimally penetrates a biological material and only sterilizes its surface. Thus, ultraviolet light is unable to sterilize three-dimensional and opaque biological materials. (4) Sterilization with chemical reagents, as disclosed in U.S. Pat. Nos. 5,460,962 and 6,096,266, as well as Taiwan Pat. Nos. 310,308, 241,193, and 149,465: this method is carried out by adding a chemical bactericide into a biological material. However, chemical bactericides are not widely applied as they are toxic and difficult to remove from biological materials sterilized therewith. (5) Sterilization under high temperature and high pressure (autoclave), as disclosed in Taiwan Pat. No. 443,932: the autoclave method results in denaturation of biological materials and complete loss of their bioactivity. In sum, the aforementioned methods have respective drawbacks, which often cause biological materials to change in chemical structure and properties, resulting in loss of biocompatibility and applicability.

Ozone is typically applied in surface modification of polymeric biomaterials. Ozonation generates activated peroxides on the surface of a biomaterial, and it further induces graft copolymerization with certain functional groups on the biomaterial and its degradation in aqueous environments. Ozone is used for sterilization of general instruments as disclosed in U.S. Pat. No. 5,788,941 and Taiwan Pat. No. 061,995. This method is accomplished by placing the instrument into an ozone-containing environment. In general, a biological material contains some water or even exists in a solubilized state. The aqueous content in a biological material may react with ozone gas, causing changes in chemical functional groups inside the biological material, and even micro-changes inside the structures of the biological material, such as polymerization and degradation, thereby affecting physiochemical properties of the biological material. Further, for a solubilized biological material, ozone dissolved in the solution may be insufficient to achieve desirable sterilizing effect.

For the foregoing reasons, it is necessary to develop a method for sterilizing biological materials that does not compromise their bioactivity and structure.

SUMMARY OF THE INVENTION

The present invention relates to a novel method for sterilizing a biological material, which overcomes the shortcomings of ozone sterilization methods described in the prior art, i.e., degradation of the biological material and insufficient ozone for sterilization.

According to one embodiment of the present invention, a method for sterilizing biological materials is provided as follows. A dehydrated biological material is put into a closed container. The closed container is then decompressed under a vacuum. Subsequently, 0.01 $g/m^3$ to 1000 $g/m^3$ of a sterilizing gas, i.e., pure ozone, is introduced into the container for a period of time until the biological material is sterilized.

In an embodiment of this method, the biological material is dehydrated by lyophilization.

Optionally, the method further includes the step of removing the sterilizing gas from the closed container after the dehydrated biological material is sterilized. This step can be carried out by vacuum degassing or standing degassing.

The details of the invention are set forth in the description below. Other features, objects, and advantages of the invention will be apparent from the following detailed description of several embodiments, and also from the appending claims.

BRIEF DESCRIPTION OF THE DRAWINGS

The description below refers to the accompanying drawings, of which.

DETAILED DESCRIPTION

Figure 1:
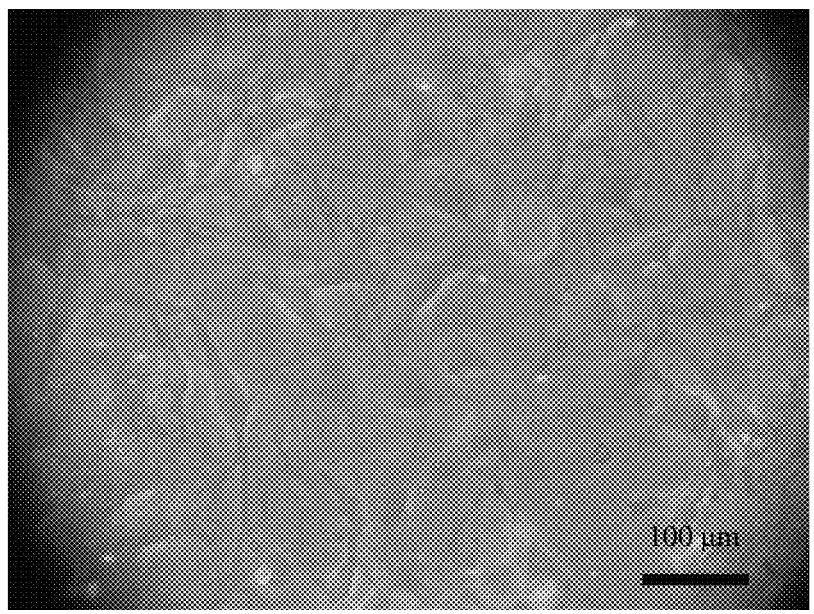
FIG. 1 is a micrograph at 100 times magnification showing the morphology of fibroblasts cultured on a collagen matrix sterilized by the present method.

The description below providing various embodiments and specific details of the invention is illustrative only and should not be construed in any way as limiting the invention. Furthermore, various applications of the invention, and modifications thereto, which may occur to those who are skilled in the art, are also encompassed by the general concepts described below.

The present invention provides a method for sterilizing biological materials. In one embodiment, the method for sterilizing biological materials is performed as follows. After dehydrating the biological material, the dehydrated biological material is put into a closed container, and 0.01 g/m$^3$ to 1000 g/m$^3$ or an enough dose of ozone gas is introduced into the container for a period of time until the biological material is completely sterilized. Afterwards, the ozone gas is removed from the closed container to finish sterilization of the biological material.

An "enough dose" refers to a dose of ozone gas that is able to achieve complete sterilization of a biological material and can be changed according to the amount of biological material to be sterilized and the volume of the closed container. The term "biological material" refers to a material existing in a living organism, a material produced by a living organism, or a material for use in a living organism. For example, the biological material can be a growth factor, an antibody, a hormone, a protein drug, collagen, gelatin, a lipid, a fat, a ribonucleotide, a deoxyribonucleotide, a ribonucleic acid, a deoxyribonucleic acid, a saccharide, an oligosaccharide, a polysaccharide, hyaluronan, elastin, chondroitin sulfate, heparin, heparan sulfate, dermatan sulfate, glycosaminoglycan, chitin, chitosan, alginate, or a related derivative thereof that exists in a living organism. Moreover, the biological material can also be an enzyme, a protein product, a protein drug, a cell culture material with a biological component, an extracellular matrix, a matrix for medical use, an artificial tissue, an organ, a genetic-engineering product, a material of Chinese herb medicine, a product of Chinese herb medicine, a cosmetic product, or a cosmetic additive produced by a living organism. Furthermore, the biological material can be an antibiotic, a cell culture material with a biological component, an extracellular matrix, a matrix for medical use, an artificial tissue, or an organ for use in a living organism.

The present invention is characterized by removing water from a biological material, so as to prevent the shortcomings in the prior art, such as undesired reaction between ozone and water, or insufficient ozone content in water. Even though one skilled in the art commonly knows the methods and conditions how to remove water, the present method can remove water without substantially affecting inherent bioactivity and physiochemical properties of the biological material. According to an embodiment of the present invention, the biological material is dehydrated by lyophilization. According to another embodiment of the present invention, the biological material is dehydrated under low temperature and decreased pressure.

According to the present method, the dehydrated biological material is put into a closed container for sterilization with ozone. The closed container of the present invention is suitable for receiving the biological material, and it is beneficial to supply ozone gas therein or exhaust ozone gas therefrom. Preferably, the closed container has a channel for supplying and exhausting ozone.

The enough dose of ozone required for sterilization depends on the quantity and property of the biological material. Typically, the ozone concentration is in the range of 0.01 g/m$^3$ to 1000 g/m$^3$. Preferably, the concentration is in the range of 1 g/m$^3$ to 50 g/m$^3$. The period of sterilization also depends on the quantity and property of the biological material. For example, 30 minutes may be needed for sterilizing collagen.

According to the present method, the ozone gas is then removed from the closed container. One skilled in the art commonly knows the methods how to remove the ozone gas. In a preferred embodiment of the present invention, the ozone gas is removed by vacuum degassing, sterile gas exchange, or standing degassing.

The present invention further provides another method for sterilizing collagen. In one embodiment, the method for sterilizing collagen is performed as follows. After dehydrating collagen, the dehydrated collagen is put into a closed container, and 0.01 g/m$^3$ to 1000 g/m$^3$ or an enough dose of ozone gas is introduced into the container for a period of time until the collagen is completely sterilized. Afterwards, the ozone gas is removed from the closed container.

Without further elaboration, it is believed that one skilled in the art can, based on the above description, utilize the present invention to its fullest extent. The following specific examples are, therefore, to be construed as merely illustrative, and not limitative of the remainder of the disclosure in any way whatsoever. All of the publications cited herein are incorporated by reference.

Example 1: Sterilization of Collagen

A collagen solution was lyophilized to obtain dehydrated collagen. Subsequently, the dehydrated collagen thus obtained was put into a closed container (21 cm×15 cm×7 cm), after which 120 mg/hour (approximately 27.2 g/m$^3$) of pure ozone gas was introduced into the container for approximately 30 minutes. Before introducing pure ozone, the container was optionally decompressed under a vacuum. The ozone gas that remained in the collagen was then removed by standing at a ventilated laminar flow stage for about 1 hour at room temperature, or alternatively, vacuuming for 1 hour, so as to finish sterilization of the biological material. During sterilization, except pure ozone, no other gases were introduced into the container.

Example 2: Effect of Ozone Sterilization on Collagen

Studies were conducted to compare collagen sterilized with ozone to that sterilized by conventional ultra-high-speed centrifugation. Unsterilized collagen was included as the control.

Cell morphology on sterilized collagen: human foreskin fibroblasts were seeded on collagen matrices sterilized by the procedure described in Example 1 or conventional ultra-high-speed centrifugation. Cell morphologies were observed under a light microscope and photographed under 100 times magnification. As shown in FIG. 1, the morphology of fibroblasts grown on the collagen matrix sterilized by ozone gas are similar to that of fibroblasts grown on the collagen matrix sterilized by conventional ultra-high-speed centrifugation (not shown), in which microorganisms deposited as a sediment and were removed.

Total cell numbers: human foreskin fibroblasts were seeded with a collagen solution sterilized by centrifugation, with a collagen solution sterilized by ozone gas, on a collagen matrix sterilized by centrifugation, and on a collagen matrix sterilized by ozone gas. Dulbecco's Modified Eagle's Medium (DMEM) supplemented with 10 vol. % fetal bovine serum (FBS) was used to culture the fibroblasts. After a period of incubation, the collagen matrix was digested with collagenase, and the total cell numbers were counted to determine the percentages of cell numbers in comparison to the control. The results are shown in Table 1 below.

TABLE 1

| Treatment of Collagen | Total Cell Number (%) |
| --- | --- |
| Collagen solution sterilized by conventional centrifugation | 100 ± 4.3 |
| Collagen solution sterilized by ozone gas | 96 ± 4.3 |
| Collagen matrix sterilized by conventional centrifugation | 100 ± 3.4 |
| Collagen matrix sterilized by ozone gas | 106 ± 8.6 |

The results in Table 1 indicate that growth of fibroblasts cultured on the collagen matrix or with collagen solution, sterilized by ozone gas or conventional centrifugation, is very similar.

Integrity of collagen molecule: molecular integrity was examined for collagen in an ozone-sterilized collagen solution and that in an ozone-sterilized dehydrated collagen matrix. After sterilization with ozone, the collagen solution became more viscous, indicating that ozone sterilization caused some polymerization when performed on collagen with high water content. By contrast, ozone sterilization caused no structural change on the dehydrated collagen matrix. Thus, it can be seen that the dehydrating step is a key step of the present method.

Sterilizing ability: collagen solutions (unsterilized or ozone-sterilized) and dehydrated collagen matrices (unsterilized or ozone-sterilized) were mixed with *Staphylococcus aureus* (ATCC-25178) in Luria-Bertani (LB) broth. After culturing for 16 hours, turbidity of the cultures was monitored at 600 nm (OD600).

Figure 2:
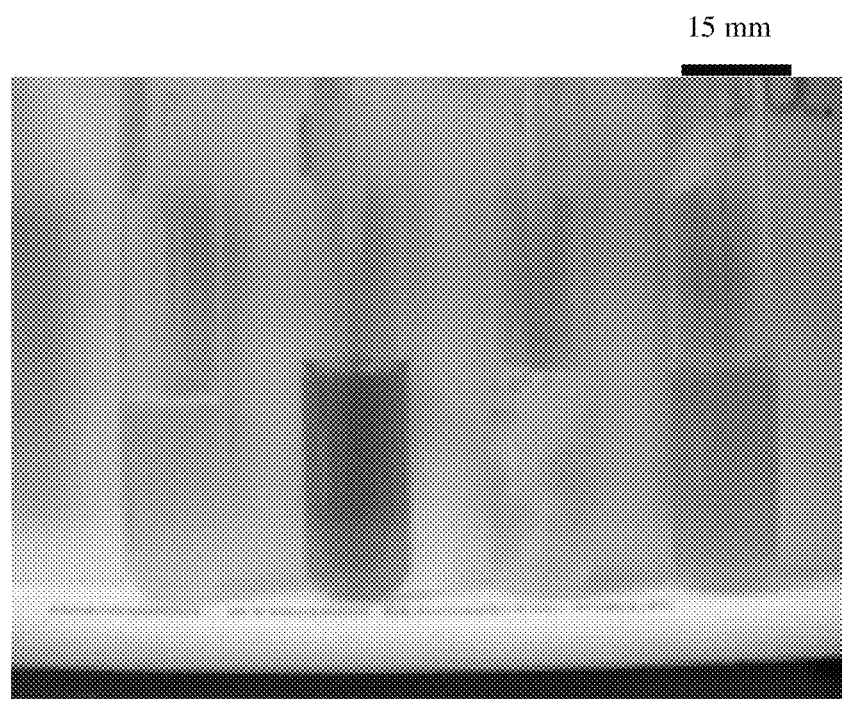
FIG. 2 is a photo of culture tubes incubated for 16 hours. Each of the culture tubes contains Staphylococci cultured in LB broth respectively mixed with, from left to right, an unsterilized collagen matrix, an ozone sterilized collagen matrix, an unsterilized collagen solution, and an ozone sterilized collagen solution.

Reference is made to FIG. 2, which shows culture tubes wherein *Staphylococcus aureus* was cultured in LB broth respectively mixed with, from left to right, an unsterilized collagen matrix, an ozone-sterilized collagen matrix, an unsterilized collagen solution, and an ozone sterilized collagen solution. It can be seen that the culture incubated with the unsterilized collagen matrix and that incubated with the unsterilized collagen solution were turbid due to Staphylococci growth. On the other hand, the culture incubated with the sterilized collagen matrix and that incubated with the sterilized collagen solution were clear. The OD600 data obtained for each of the four samples is shown in Table 2 below.

TABLE 2

|  |  | OD600 |
| --- | --- | --- |
| Dehydrated collagen matrix | Unsterilized | 1.1886 |
|  | Ozone-sterilized | 0.0710 |
| Collagen solution | Unsterilized | 2.0302 |
|  | Ozone-sterilized | 0.6288 |

As shown in Table 2, the samples containing unsterilized collagen had substantially higher OD600 values, which correlated to more Staphylococci growth, as compared to the samples containing ozone-sterilized collagen. These results demonstrate that ozone treatment is effective in sterilizing both dehydrated collagen matrices and collagen solutions.

Molecular Property of Sterilized Collagen: equivalent amounts of dehydrated collagen were subjected to the following respective treatments: (1) non-treatment; (2) treatment with ozone gas, as described in Example 1; (3) treatment with ultraviolet irradiation for 12 hours; (4) immersion in 75 vol. % ethanol for 4 hours; (5) immersion in 2 vol. % formaldehyde for 1 hour; or (6) autoclave sterilization under high-temperature and high-pressure. Afterwards, each of the samples from the aforementioned treatments was dissolved in acetate solution, analyzed by 5% acrylamide gel electrophoresis, and stained with Coomassie blue. The results are shown in FIG. 3.

Figure 3:
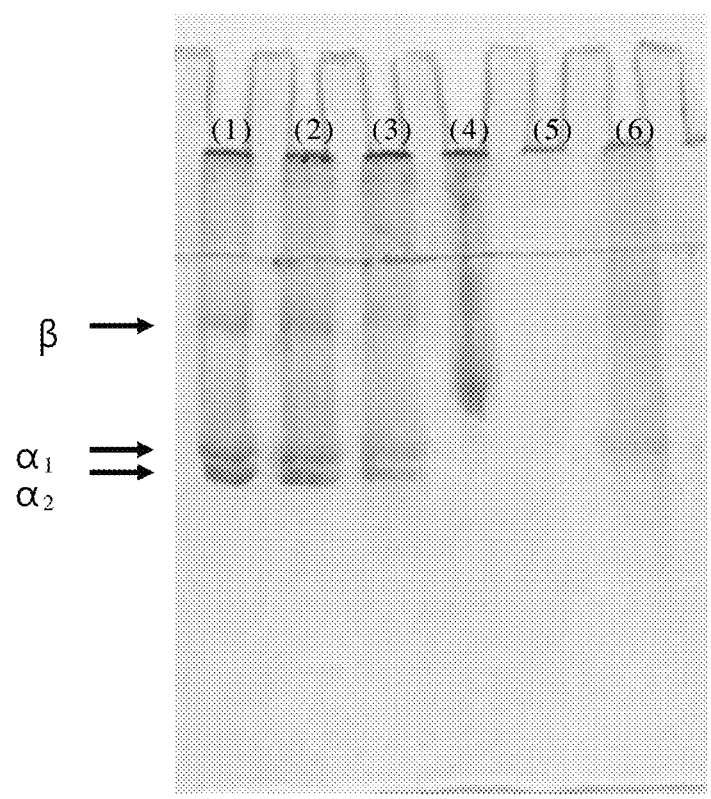
FIG. 3 is a stained electrophoresis gel of collagen subjected to the following procedures: (1) non-treatment; (2) treatment with ozone; (3) treatment with ultraviolet irradiation for 12 hours; (4) immersion in 75 vol. % ethanol for 4 hours; (5) immersion in 2 vol. % formaldehyde for 1 hour; and (6) autoclave sterilization.

Reference is made to FIG. 3. The dehydrated collagen treated by ozone gas [lane (2)] shows bands of the major α1, α2 and β chains that are substantially the same as the control [lane (1)], indicating that the molecular weights and ratios of these components were unchanged; the collagen treated by ultraviolet irradiation [lane (3)] was partially polymerized and cleaved, as evidenced by decrease in stain density of the α1, α2 and β bands; the collagen treated by immersion in ethanol [lane (4)] only showed indistinct bands in the electrophoresis gel as its components were polymerized and therefore less soluble; the collagen treated by immersion in formaldehyde [lane (5)] showed no bands in the electrophoresis gel as its components were highly polymerized and insoluble, resulting in their inability to enter the gel; the collagen treated by autoclave sterilization under conventional high-temperature and high-pressure [lane (6)] was mostly degraded and therefore showed major bands with decreased stain density. It is clear that the ozone sterilization method is better than other methods for treating collagen.

Example 3: Effect of Ozone Sterilization on Riboflavin

Dehydrated riboflavin was untreated, sterilized by autoclave, or sterilized with ozone. Samples were then dissolved in water to prepare six riboflavin solutions, i.e., solution 1 (100 mg/mL, autoclaved), solution 2 (100 mg/mL, ozone-sterilized), solution 3 (100 mg/mL, untreated), solution 4 (50 mg/mL, autoclaved), solution 5 (50 mg/mL, ozone-sterilized), and solution 6 (50 mg/mL, untreated). Fluorescence intensities of the six solutions were observed under ultraviolet irradiation.

Figure 4:
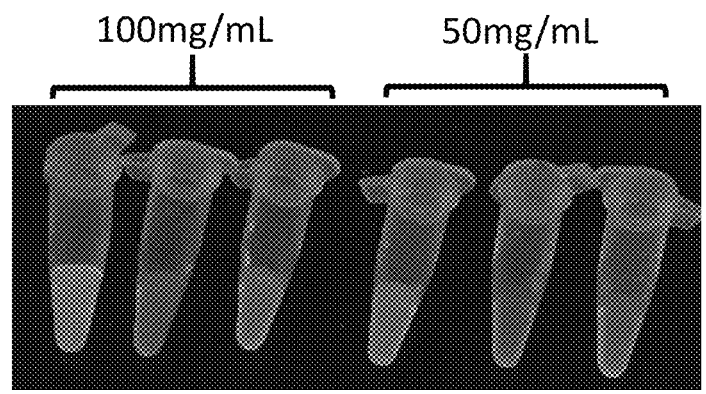
FIG. 4 is a photo of microcentrifuge tubes, irradiated with ultraviolet light, containing aqueous solutions (100 mg/mL or 50 mg/mL) of riboflavin: (1) 100 mg/mL, autoclaved; (2) 100 mg/mL, ozone-treated; (3) 100 mg/mL, untreated; (4) 50 mg/mL, autoclaved; (5) 50 mg/mL, ozone-treated; and (6) 50 mg/mL, untreated.

As shown in FIG. 4, fluorescence intensities of the autoclaved riboflavin solutions, i.e., solutions 1 and 4, were higher than those of the untreated control solutions, i.e., solutions 3 and 6. The higher fluorescence intensities of solutions 1 and 4 were attributed to higher degrees of degradation of the autoclave riboflavin. By contrast, fluorescence intensities of solutions containing ozone-sterilized riboflavin, i.e., solutions 2 and 5, were similar to those of the untreated riboflavin solutions, which indicated that riboflavin remained intact after being sterilized with ozone. In view of these results, it is clear that ozone is superior to autoclave for sterilizing riboflavin.

Example 4: Effect of Ozone Sterilization on Pepsin and Bromelain

Samples of two dehydrated enzymes, i.e., pepsin and bromelain, were untreated, sterilized by autoclave, or sterilized with ozone. Subsequently, the samples were dissolved acetate solutions, analyzed by 5% acrylamide gel electrophoresis, and stained with Coomassie blue.

Figure 5:
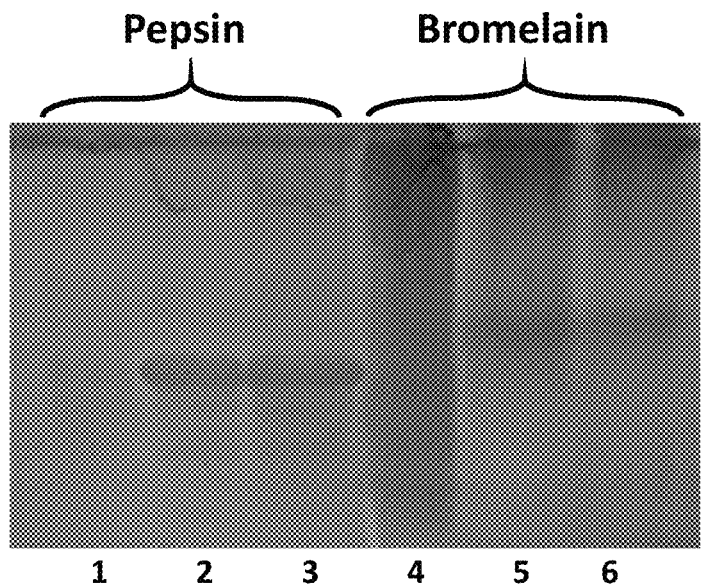
FIG. 5 is a stained electrophoresis gel of pepsin and bromelain subjected to three different procedures: (1) pepsin, autoclave sterilization; (2) pepsin, treatment with ozone; (3) pepsin, non-treatment; (4) bromelain, autoclave sterilization; (5) bromelain, treatment with ozone; and (6) bromelain, non-treatment.

Reference is made to FIG. 5. As seen in this figure, ozone-treated pepsin [lane (2)] showed a single band that was the same as that shown by untreated pepsin [lane (3)], indicating that ozone did not degrade this enzyme. On the other hand, autoclaved pepsin [lane (1)] showed a band with substantially reduced stain density, indicating degradation of the enzyme. Ozone-treated bromelain [lane (5)] showed the same band as the control [lane (6)], indicating that this enzyme also was not degraded by ozone. By contrast, autoclaved bromelain [lane (4)] only showed an indistinct band, signifying a high degree of degradation. It is clear that ozone-sterilization, unlike autoclave-sterilization, does not affect molecular integrity of both pepsin and bromelain.

Example 5: Effect of Ozone Sterilization on Hyaluronan

Two equivalent amounts of hyaluronan (average molecular weight: 58 kDa), were respectively subjected to ozone sterilization and autoclave sterilization. Subsequently, the sterilized samples were analyzed by capillary electrochromatography using a fused silica capillary and a 50 mM phosphate buffer (pH 2.99). Separations were carried out at 25 kV and a column temperature of 25° C. Absorbance was detected at 194 nm. Shown in Table 3 below are the areas under the peak for each of the two samples, which correspond to the amount of hyaluronan contained therein. An untreated sample was included as the control.

TABLE 3

| Sample | Migration Time (min.) | Area under the Peak |
| --- | --- | --- |
| Autoclaved | 12.179 | 633930 |
| Ozone-treated | 12.179 | 814725 |
| Untreated control | 12.358 | 874193 |

As shown in Table 3, the area under the peak for the ozone-treated sample (814725) was similar to that of the untreated control (874193). On the other hand, the peak area of the autoclaved sample was reduced (633930). These results demonstrate that ozone-sterilization causes less material loss as compared to autoclave-sterilization.

OTHER EMBODIMENTS

As is understood by a person skilled in the art, the foregoing descriptions of the embodiments of the present invention are an illustration of the present invention rather than a limitation thereof. Various modifications and similar arrangements are included within the spirit and scope of the appended claims. The scope of the claims should be accorded to the broadest interpretation so as to encompass all such modifications and similar structures. While an embodiment of the invention has been illustrated and described, it will be appreciated that various changes can be made therein without departing from the spirit and scope of the invention.

The invention claimed is:

1. A method for sterilizing a biological material, comprising:
   obtaining a dehydrated biological material;
   putting the dehydrated biological material into a closed container in the absence of water;
   decompressing the closed container under a vacuum; and
   introducing 0.01 g/m$^3$ to about 1000 g/m$^3$ of a sterilizing gas, without introducing any other gases, into the closed container in the absence of water for a period of time until the dehydrated biological material is sterilized,
   wherein the sterilizing gas is ozone, and the dehydrated biological material substantially remains intact after sterilization.

2. The method of claim 1, wherein the biological material is a material produced by a living organism.

3. The method of claim 2, wherein the biological material is dehydrated by lyophilization.

4. The method of claim 2, further comprising a step of removing the sterilizing ozone gas from the closed container after the dehydrated biological material is sterilized.

5. The method of claim 4, wherein the step of removing the sterilizing gas from the closed container is carried out by vacuum degassing.

6. The method of claim 4, wherein the step of removing the sterilizing gas from the closed container is carried out by standing degassing.

7. The method of claim 1, wherein the biological material is a material for use in a living organism.

8. The method of claim 7, wherein the biological material is dehydrated by lyophilization.

9. The method of claim 7, further comprising a step of removing the sterilizing gas from the closed container after the dehydrated biological material is sterilized.

10. The method of claim 9, wherein the step of removing the sterilizing gas from the closed container is carried out by vacuum degassing.

11. The method of claim 9, wherein the step of removing the sterilizing gas from the closed container is carried out by standing degassing.

12. The method of claim 1, further comprising a step of removing the sterilizing gas from the closed container after the dehydrated biological material is sterilized.

13. The method of claim 12, wherein the step of removing the sterilizing gas from the closed container is carried out by vacuum degassing.

14. The method of claim 12, wherein the step of removing the sterilizing gas from the closed container is carried out by standing degassing.

15. The method of claim 1, wherein the biological material is a growth factor, an antibody, a hormone, a protein drug, an enzyme, collagen, a collagen derivative, gelatin, a gelatin derivative, a lipid, a fat, a ribonucleotide, a deoxyribonucleotide, a ribonucleic acids, a deoxyribonucleic acid, a saccharide, an oligosaccharide, a polysaccharide, hyaluronan, elastin, chondroitin sulfate, heparin, heparin sulfate, dermatan sulfate, glycosaminoglycan, chitin, chitosan, or alginate.

16. The method of claim 1, wherein the biological material is a biological matrix.

17. The method of claim 16, wherein the biological material is dehydrated by lyophilization.

18. The method of claim 16, further comprising a step of removing the sterilizing gas from the closed container after the dehydrated biological material is sterilized.

19. The method of claim 18, wherein the step of removing the sterilizing gas from the closed container is carried out by vacuum degassing.

20. The method of claim 18, wherein the step of removing the sterilizing gas from the closed container is carried out by standing degassing.

* * * * *